United States Patent [19] … [11] 4,072,569
Box … [45] Feb. 7, 1978

[54] **PREPARATION OF CLAVULANIC USING *STREPTOMYCES JUMONJINENSIS***

[75] Inventor: Stephen John Box, Roffey, England

[73] Assignee: Beecham Group Limited, United Kingdom

[21] Appl. No.: 726,135

[22] Filed: Sept. 24, 1976

[30] Foreign Application Priority Data

Oct. 29, 1975 United Kingdom ............... 41898/75

[51] Int. Cl.² ............................................... C12D 9/14
[52] U.S. Cl. ................................................. 195/80 R
[58] Field of Search ..................... 195/80 R, 96, 36 R, 195/36 P, 47, 42

[56] References Cited

U.S. PATENT DOCUMENTS 3,865,693  2/1975  Arai et al. .......................... 195/80 R

OTHER PUBLICATIONS

Cole et al., "Antibacterial Clavulanic Acid, its Salts and Esters", *Chemical Abstracts*, vol. 84, No. 11, (1976), p. 322.

*Primary Examiner*—Raymond N. Jones
*Assistant Examiner*—Thomas G. Wiseman
*Attorney, Agent, or Firm*—Jacobs & Jacobs

[57] ABSTRACT

Clavulanic acid and its salts may be produced by cultivating a strain of *Streptomyces jumonjinensis*.

20 Claims, No Drawings

PREPARATION OF CLAVULANIC USING STREPTOMYCES JUMONJINENSIS

The present invention relates to the production of clavulanic acid and its salts via fermentation of *Streptomyces jumonjinensis*.

Clavulanic acid, which is the useful antibacterial compound of the formula (I):

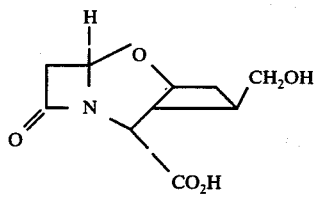

and its salts and esters are described in Belgian Pat. No. 827926. Belgian Pat. No. 827926 also describes the preparation of clavulanic acid and its derivatives via fermentation of *Streptomyces clavuligerus*.

*Streptomyces jumonjinensis* has been described in Belgian Pat. No. 804341 as producing an antibacterial agent other than clavulanic acid. It has now been discovered that clavulanic acid is also produced during the cultivation of *Streptomyces jumonjinensis*.

Accordingly the present invention provides a process for the preparation of clavulanic acid and its salts which process comprises cultivating a strain of *Streptomyces jumonjinensis* and recovering clavulanic acid or salt thereof from the culture.

Suitably the clavulanic acid is recovered as its solid lithium, sodium, potassium, calcium, magnesium, barium, aluminium, ammonium or substituted ammonium salts. Suitably substituted ammonium salts include primary, secondary, tertiary and quaternary ammonium salts.

Suitably clavulanic acid is recovered as its solid alkali metal salt such as its sodium or potassium salt.

By the term solid salts of clavulanic acid we mean crystalline salts and amorphous salts of clavulanic acid. Conveniently the salts of the clavulanic acid are obtained as crystalline salts for example as the sodium clavulanate tetrahydrate crystalline salt or the crystalline potassium or lithium salts.

Preferably *Streptomyces jumonjinensis* NRRL 5741 or a high yielding mutant thereof is used in the process of this invention.

*Streptomyces jumonjinensis* NRRL 5741 has also been deposited at Baarn the Netherlands as CBS 177.76 and at the German collection of Microorganisms DSN.

When used herein the term cultivation means the deliberate aerobic growth of a clavulanic acid producing organism in the presence of assimilable sources of carbon, nitrogen and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

Belgian Pat. No. 804,341 describes general conditions for the cultivation of *Streptomyces jumonjinensis*.

I have found media containing complex nutrients such as yeast extract, soya bean flour and the like to be particularly suitable.

The nutrient media which may be used for the cultivation of *Streptomyces jumonjinensis* may contain, in the range 0.1 – 10% a complex organic nitrogen source such as yeast extract, corn steep liquor, vegatable protein, seed protein, hydrolysates of such proteins, milk protein hydrolysates, fish and meat extracts and hydrolysates such as peptones. Alternatively chemically defined sources of nitrogen may be used such as urea, ammonium salts, amides, single or mixtures of common amino acids such as valine, asparagine, glutamic acid proline and phenylalanine. Carbohydrate (0.1 – 5%) may be included in the nutrient media. Starch or starch hydrolysates such as dextrin, sucrose, lactose or other sugars or glycerol or glycerol esters may also be used. The sources of carbon may also be derived from vegetable oils or animal fats. Carboxylic acids and their salts can be included as a source of carbon for growth and production of $\beta$-lactamase inhibitors.

The addition of antifoam agents (such as Pluronic L81) may be necessary to control foaming of certain media in fermenters.

Mineral salts such as $NaCl$, $KCl$, $MgCl_2$, $ZnCl_2$, $FeCl_3$, $Na_2SO_4$, $FeSO_4$, $MgSO_4$. and $Na^+$ or $K^+$ salts of phosphoric acid may be added to the media described above, particularly if chemically defined; $CaCO_3$ may be added as a source of $Ca^{++}$ ions or for its buffering action. Salts of trace elements such as nickel, cobalt or manganese may also be included. Vitamins may be added if desired.

When used herein the term mutant includes any mutant strain which arises spontaneously or through the effect of an external agent whether that agent is applied deliberately or otherwise. Suitably methods of producing mutant strains include those described in Belgium Pat. No. 827,926.

Cultivation of *Streptomyces jumonjinensis* normally takes place in the temperature range 16° – 35° C usually 20° – 32° C and preferably 25° – 30° C, for example at about 27° C and at a pH of between 5 and 8.5, and more suitably between 6 and 7.5.

The *Streptomyces jumonjinensis* may be cultivated in the above media in conventional vessels such as glass conical flasks aerated by agitation, for example by shaking on a rotary shaker, or in aerated fermenters, for example in baffled stainless steel fermenters stirred with vaned disc impellers and aerated with a sparger. The fermentation may also be carried out in a continuous fashion.

The starting pH of the fermentation is typically 7.0 and maximum yield of clavulanic acid is obtained in 1 –10 days at 20° – 32° C, for example in 2 – 5 days.

Clavulanic acid as its salts may be extracted from culture filtrate by a variety of methods such as those described in Belgian Pat. No. 827,926. Solvent extraction from cold culture filtrate adjusted to acid pH values and methods based on the anionic nature of the metabolite such as the use of anion exchange resins have been found to be particulary useful. The cells of the *Streptomyces jumonjinensis* are normally first removed from the fermentation by filtration or centrifugation before such extraction procedures are commenced.

In the solvent extraction process the culture filtrate is chilled and the pH lowered into the region of pH 2–3 by the addition of acid while thoroughly mixing with a water immiscible organic solvent such as n-butylacetate, methylisobutylketone, n-butanol or ethylacetate. The acid used to lower the pH of the medium is normally a mineral acid such as hydrochloric sulphuric, nitric, phosphoric or the like acid. n-Butanol is a particularly suitable solvent for use in the extraction of the acidified culture filtrate. After separation of the phases by centrifugation, the clavulanic acid metabolite is back extracted from the solvent phase into aqueous sodium bicarbonate or potassium hydrogen phosphate buffer, $CaCO_3$ suspension or water while maintaining the pH at approximate neutrality, for example, at pH 7.0. This aqueous extract after separation of phases may be concentrated under reduced pressure and freeze dried to give a crude preparation of a salt of clavulanic acid. This preparation is stable when stored as a dry solid at $-20°$ C.

In the anion exchange resin process, the culture filtrate at an approximately neutral or slightly acid pH, for example pH 6-7 is contacted with a bed of weak or strong base anion exchange resin such as Amberlite IR4B or Zerolit FFIP respectively usually until the resin is saturated and the clavulanic acid material emerges from the bed. The bed is then washed with water and eluted with an aqueous salt solution such as an alkali metal chloride, for example sodium chloride. The clavulanic acid containing fractions are collected, bulked, desalted and freeze dried to yield a crude solid salt of clavulanic acid. Amberlite IR4B is an example of a weakly basic anion exchange resin with polyamine active groups and cross linked polystyrene -divinyl-benzene matrix. Other suitable weakly basic anion exchange resins include Amberlite IRA68 and IRA93. Zerolit FFIP is a strongly basic anion exchange resin with quaternary ammonium active groups and a cross linked polyvinyl-divinylbenzene matrix. Resins equivalent to Zerolit FFIP include Isopor FFIP and DeAcidite FFIP SRA 64, 61 and 62.

An alternative form of the extraction process is to contact the culture filtrate (usually at approximately neutral pH) containing a salt of clavulanic acid with an organic phase in which is dissolved a water insoluble amine. Suitable organic solvents include such conventional water immiscible polar solvents as methylisobutylketone, trichloroethylene and the like. Suitable amines include secondary or tertiary amines in which one of the substitient groups is a long chain aliphatic group, for example of 12-16 carbon atoms, and the other is a tertiaryalkyl group so that the molecule is lipophilic. In our hands Amberlite LA2 has proved a successful amine. Normally the amine is used as its acid additional salt. After this extraction process the clavulanic acid is present in the organic phase as the amine salt. The organic phase is then separated from the culture filtrate. The clavulanic acid may be extracted into an aqueous solution of an alkali metal salt such as sodium chloride, sodium nitrate or the like. The crude salt of clavulanic acid may then be obtained by freeze drying or the like.

Other primary methods of isolation which may be used include conventional methods such as adsorption onto carbon, precipitation, salting out and molecular filtration. These methods will normally be used in conjunction with other isolation methods.

Adsorption onto carbon may suitably be effected by passing an aqueous solution of culture filtrate through a charcoal bed, for example down a column containing charcoal. The charcoal bed is then suitably washed with water and the bed is then eluted with an aqueous water miscible solvent, such as a ketone for example acetone and the clavulanic acid containing fractions retained. It is often convenient to elute firstly with acetone and then with aqueous acetone.

It may often be convenient to prepare clavulanic acid as a relatively water-insoluble salt, such as the lithium salt. In this case precipitation and salting out are useful methods of preparation. Precipitation may conveniently be carried out by adding a water insoluble organic solvent to an aqueous solution of the relatively water insoluble salt of clavulanic acid, for example lithium clavulanate. This process may suitably be effected by contacting a salt of clavulanic acid with a lithium salt, either by elution from a column or by dissolving the salts in the same solution and adding the water-miscible solvent to the solution containing lithium clavulanate, thereby precipitating lithium clavulanate.

Lithium clavulanate may be salted out of an aqueous solution containing lithium clavulanate in the presence of an ionic lithium compound, which is conveniently the lithium salt used to form the lithium clavulanate, by raising the concentration of lithium ions in solution so that the solubility of lithium clavulanate at the temperature concerned is greatly exceeded. Since lithium clavulanate is less soluble at lower temperatures this process is suitably effected at a depressed temperature for example 0°-5° C.

Further purification of the crude solids obtained by methods described above may be obtained by a variety of methods but ion exchange column chromatography is particularly suitable especially when using Isopor, DeAcidite FFIP SRA64 or DEAE cellulose. The DeAcidite column may be gradient eluted with an aqueous solution of a salt such as sodium chloride (0 - 0.5M). The column of DEAE cellulose in 0.01M phosphate buffer at pH7 may be eluted with a salt solution normally an alkali metal chloride solution such as NaCl solution (0-0.2M NaCl in 0.01M phosphate buffer pH7). Active fractions may be detected by their β-lactamase inhibitory activity and their activity on the KAG system both of which are described in Belgian Pat. No. 827,926.

The fractions containing the bulk of this activity are then combined and concentrated to a small volume under vacuum and desalted.

Separation of clavulanic acid and/or its salts from inorganic salts in particular, but also from other contaminating substances, may be achieved by adsorbing the antibacterial onto a lipophilic resin to which inorganic salts are not adsorbed. In our hands a polystyrene-divinylbenzene copolymer such as Amberlite XAD-4 is particularly suitable, the desired antibiotic may be removed from the column by elution (elution with water or aqueous alkanol) and the resulting solution concentrated by evaporation and freeze dried to yield a material of improved purity. Separation of clavulanic acid and/or its salts from inorganic salts may also suitably be carried out by chromatography on a column composed of a gel filtration agent for exampe cross-linked dextran gels such as Sephadex G15 and poly-acrylamide gels such as Biogel P2.

(Biogel P2, Sephadex G15 and Amberlite XAD-4 are supplied by Bio Rad, Richmond, U.S.A., Pharmacia Great Britain Ltd.; 75 Uxbridge Road, London W.5., U.K. and Rohm and Haas, Philadelphia U.S.A. respectively).

Active desalted material may be further purified by chromatography, for example or a cellulose column using an aqueous alcohol solvent system, for example butanol/ethanol/ water, 4/1/5 v/v top phase.

A variation of the process for the preparation of a pure form of clavulanic acid or its salts comprises obtaining an impure form of clavulanic acid or salt thereof, forming an ester of clavulanic in a conventional manner, purifying the ester and thereafter regenerating clavulanic acid or a salt thereof from the ester. Suitably the ester for use in this aspect of the invention is the benzyl or like hydrogenolysable ester.

The impure form of clavulanic acid or salt thereof which is to be purified in this process may be in the form of a solid or solution which will usually also contain considerable quantities of organic or inorganic impurities.

The clavulanic acid or salt thereof may be converted into an ester by the esterification reactions referred to hereinafter. The preferred method of forming the required ester of clavulanic acid is by the reaction of a salt of clavulanic acid with an esterifying agent such as a reactive halide, sulphonate ester or the equivalent reagent. Such reactions are frequently carried out in an organic solvent of high dielectric constant such as dimethylformamide, dimethylformamide/acetone, dimethylsulphoxide, N-methylacetamide, hexamethylphosphoramide and the like.

If desired the salt of clavulanic acid may be dissolved in the solvent in conventional manner or it may be bound to a polymeric support. Suitable supports for use in this process include strong base anion exchange resins, especially those possessing a macroreticular nature which permits the use of non-aqueous solvent systems. We have found Amberlyst A 26 to be suitable for this purpose. The clavulanic acid salt may be adsorbed onto the resin from the culture filtrate and the resin then suspended in dimethylformamide containing sodium iodide and benzyl bromide. The clavulanic acid may alternatively be eluted column wise with a solution of sodium iodide in dimethylformamide or in a mixture of dimethylformamide and acetone. The clavulanic acid in the eluate is then esterified by addition of benzyl bromide.

Once formed, the impure ester of clavulanic acid is normally purified chromatographically. In such procedures the ester is normally dissolved in an organic solvent such as ethyl acetate, methylene chloride, chloroform, or similiar solvents. The solid phase used in the chromatographic process is normally a material such as silica gel or a gel filtration agent, such as Sephadex LH20 or chromatographically similiar materials.

The fractions emerging from the column may be tested for the presence of the clavulanic acid ester by making use of its synergistic properties or by chemical tests such as reaction with triphenyltetrazolium chloride in conjunction with thin layer chromatography. Active fractions are normally combined and the organic solvent evaporated off under reduced pressure.

The ester resulting from this process is generally of acceptable purity, but the material may be rechromatographed if desired.

This purified ester of clavulanic acid may be converted to clavulanic acid or a salt thereof by the methods described in Belgian Pat. No. 827926.

A particularly suitable method of re-obtaining clavulanic acid or its salts is by hydrogenation of its benzyl ester. Such reactions normally take place in the presence of a transition metal catalyst using low or medium pressures of hydrogen. The reaction may be carried out at a high, ambient or depressed temperature, for example at 0° – 100° C. Particularly suitable reaction conditions for such hydrogenation will use a slightly superatmospheric pressure of hydrogen at an approximately ambient (12° – 20° C) temperature. The reaction may be carried out in conventional solvents such as lower alkanols, for example ethanol. We have found that a particularly suitable catalyst is palladium on charcoal.

If the hydrogenation is carried out in the presence of a base then a salt of clavulanic acid is produced, for example the lithium sodium or potassium salt results if the reaction is carried out in the presence of sodium or potassium hydrogen carbonate, or lithium, sodium or potassium carbonate.

The clavulanic acid or salt thereof resulting from such reaction is generally of good purity, for example at least 90% pure and usually can be produced virtually totally pure.

The following examples are illustrative of the invention.

EXAMPLE 1

*Streptomyces jumonjinensis* NRRL 5741 was grown for 7 days at 28° C on solid agar slants of the following composition:
Bacto - yeast extract (Difco) — 4.0 g/l
Bacto - malt extract (Difco) — 10.0 g/l
Bacto - dextrose (Difco) — 4.0 g/l
Dissolved in distilled water Adjust to pH 7.3 then add
Bacto - agar — 20.0 g/l Growth scraped from this slant were used directly to inoculate 100 ml of seed stage medium contained in 500 ml conical flasks closed with foam plastic plugs. The composition of the seed medium was as follows:
Tryptone (Oxoid) — 5.0 g/l
Yeast Extract — 3.0 g/l The medium was sterilised before inoculation by autoclaving at 15 lb/sq.in. at 121° C for 15 minutes. The seed stage was incubated at 26° C for 65 hours on a rotary shaker at 240 r.p.m. with 1 inch throw.

5 ml portions of the seed medium were used to inoculate 100 ml portions of fermentation medium contained in 500 ml conical flasks closed with foam plugs. Three different fermentation media were used, the composition of the media were as follows:

| Medium A | Glucose | 20 | g/l |
|---|---|---|---|
| | Soya bean flour | 10 | g/l |
| | $CaCO_3$ | 0.2 | g/l |
| | $Na_2SO_4$ | 0.5 | g/l |
| | $CoCl_2.6H_2O$ | 0.001 | g/l |
| | Made up in distilled water. | | |
| Medium B | Dextrin | 55 | g/l |
| | Soya bean flour | 20 | g/l |
| | Mollasses | 20 | g/l |
| | $NaH_2PO_4$ | 1.3 | g/l |
| | KCl | 1.0 | g/l |
| | Made up in distilled water | | |
| Medium C | Yeast extract (Oxoid) | 10 | g/l |
| | Scotasol, | 20 | g/l |
| | Made up in distilled water pH adjusted to 7 before sterilisation | | |

(The Soya Bean flour is Arkasoy 50, supplied by British Arkday Co., Old Trafford, Manchester; Scotasol is malt distillers' dried solubles, supplied by Thomas Borthwick Ltd., 69 Wellington Street, Glasgow. U.K. Dextrin is supplied by C.P.C. (U.K.) Ltd., Trafford Park, Manchester U.K.).

All fermentation media were sterilised before inoculation by autoclaving at 15 lb/sq. in. at 121° C for 15 minutes.

The fermentation flasks were incubated at 26° C on a rotary shaker at 240 r.p.m. with 1 inch throw. 5 ml samples were removed from the fermentation flasks under sterile conditions on day 2 of the fermentation and treated in the following manner.

The smaples were centrifuged at 2,200 g for 10 minutes and the supernatant retained. The supernatant was found to have inhibitory activity against a preparation of E.coli JT4 β-lactamase using a standard β-lactamase inhibition assay. A suitable β-lactamase inhibition assay is described in Belgian Pat. No. 827,926.

EXAMPLE 2

Streptomyces jumonjinensis NRRL 5741 was grown in Medium A as described in Example 1. 5 ml. Samples were withdrawn at regular intervals throughout the fermentation using sterile technique. The supernatant obtained by centrifugation of these samples at 2,200 g for 10 minutes was assayed using a number of procedures detailed below.

a. Its antibacterial activity against *Klebsiella aerogenes* A using a hole in plate agar diffusion assay.

b. Its activity on the KAG agar plate system described in Belgian Pat. No. 827926 was measured.

| Assay technique | Length of fermentation (days) | | | |
|---|---|---|---|---|
| | 2 | 3 | 4 | 7 |
| Zone diameter (mm) on Klebsiella aerogenes | — | 20.5 | 17.4 | — |
| Zone diameter (mm) in the KAG system | — | 37.1 | 26.8 | — |

Samples from day 4 of this fermentation were spotted on 1 cm wide strips of Whatman No. 1 chromatography paper. These strips were chromatographed overnight at 4° C in the following solvent systems:

n-Butanol/ethanol/water 4:1:5 v/v (top phase)
n-Butanol/acetic acid/water 12:3:5 v/v.

The tapes were dried and laid on agar plates seeded with *Klebsiella aerogenes* NCTC 418 and containing penicillin G (KAG plates). After incubation of the plates for 16 hours at 28° zones of inhibition of growth were seen. In both solvent systems a single inhibitor zone was seen at $R_F$0.72 in the butanol/acetic acid/water system and at $R_F$0.25 in butanol/ethanol/water. The $R_F$'s were the same of those of an authentic sample of clavulanic acid when run in the same system.

EXAMPLE 3

*Streptomyces jumonjinensis* NRRL 5741 was grown for 7 days at 26° C on solid agar slants contained in Roux bottles. The agar medium was:

Bacto-Yeast Malt Extract Agar (ISP-medium 2)
(Difco Laboratories, Detroit, Michigan, U.S.A.)

Sterile deionised water (100 ml.) containing 0.05% Triton X (surfactant) was added to a Roux bottle, the surface of the culture was scraped to produce a suspension of spores and myceluim. The suspension (100 ml.) was used to inoculate the seed stage medium (50 liters) contained in a 90 liter stainless steel fully baffled fermenter.

The seed stage medium had the following composition:

| | g/l |
|---|---|
| Tryptone (Oxoid) | 5.0 |
| Yeast Extract (Oxoid) | 3.0 |
| Antifoaming agent | 0.5 |

| -continued | |
|---|---|
| | g/l |
| Made up in Tap water | |

(The antifoaming agent consisted of 10% Pluronic L81 (Ugine Kuhlmann Chemicals Ltd) dispersed in soya bean oil (British Oil & Cake Mills).

The medium was steam sterilised in the fermenter before inoculation.

After inoculation the seed stage was agitated using a 5 inch diameter vaned disc impeller, driven at 240 r.p.m., sterile air was suppplied at 50 liters/minute and the temperature maintained at 26° C. Growth of the seed stage was continued for 48 hours.

7.5 liters of the seed stage was used to inoculate 150 liters of the fermentation medium contained in a 300 liter fully baffled stainless steel fermenter.

The fermentation stage medium had the following composition:

| | g/l |
|---|---|
| Glucose monohydrate | 20.0 |
| Soya bean flour | 10.0 |
| $CaCO_3$ | 0.2 |
| $CoCl_2.6H_2O$ | 0.001 |
| $Na_2SO_4$ | 0.5 |
| Antifoaming agent | 0.5 |
| Made up in Tap water | |

(The Soya bean flour is Arkasoy 50 supplied by British Arkady Co. Ltd., Old Trafford, Manchester).

The antifoaming agent was the same as used in the seed stage medium.

The medium was steam sterilised in the fermenter before inoculation.

After inoculation the fermentation was agitated using an 8¼ inch vaned disc impeller driven at 340 r.p.m., sterile air was supplied at 150 liters/minute and the temperature maintained at 26° throughout the 72 hour fermentation.

The whole brew was clarified by centrifugation and the clarified brew (140 L) was adjusted to pH 6.2. The clarified brew was run onto a strongly basic anion exchange resin of Zerolit FF (ip) SRA61 (15 × 130 cm) (Zerolit Ltd U.K.) at a rate of 500 ml/minute. The column was washed with chilled demineralised water (15 liters) at a flow rate of 500 ml/minute and then eluted with chilled 1M aqueous NaCl solution at the same flow rate and 4 liter fractions were collected. Fraction were monitored using the standard hole in plate bioassay technique on the KAG plate system. Fractions (2–19) giving good activity on the KAG system were combined. The combined fractions were adjusted to pH 6.2 and chilled and run onto a column of Amberlite XAD-4 (30 × 125 cm). (Rohm & Haas, Philadelphia, U.S.A.) at a rate of 500 ml/minute. The column was washed with chilled 1M NaCl (5L) and then eluted with demineralised water, at 5° C and at 500 ml/minute. 5 Liter fractions were collected starting just prior to the complete elution of the NaCl from the column. Fractions (3 – 9) containing clavulanic acid were combined.

The combined fractions (35L) were concentrated 10 fold by reverse osmosis (De Danske Sukkerfabrikker Laboratory Module, membrane type 995). The operating procedure was to recirculate the retentate from a stainless steel tank, fitted with a cooling sytem with the outlet valve of the ultrafiltration unit set so as to give a differential pressure across the 40 membranes of 45 atmospheres. The temperature was maintained at 2° - 5° C and the pH at 6.8 ± 0.1 by addition of 2NHCl. The resulting concentrate (3.5l) was dried to yield a brown amorphous solid (34 g).

2 g of this amorphous solid was purified by the method of Example 17 of Belgian Pat. No. 827926 to give substantially pure crystalline sodium clavulanate tetrahydrate. 32 g of the amorphous solid was treated with benzyl bromide (10 ml) and dimethylformamide (35 ml) and the mixture was stirred at room temperature for 4 hours. The solvents were removed in vacuo to leave a semi-solid residue. Ethyl acetate (50 ml) was added and any solid material was removed by filtration. The filtrate was evaporated in vacuo to yield an oil.

A sephadex LH20 column (3.8 × 34 cm). (Pharmacia Ltd.) was prepared in cyclohexane/chloroform 1:1. The product from the benzylation was dissolved in a minimum of cyclohexane/chloroform 1:1 and run onto the column which was eluted with the same solvent mixture. The first 150 ml of eluant were discarded and then 25 ml fractions collected. The presence of benzyl clavulanate was monitored by spotting 5μl samples from each fraction on silica gel thin layer plates and developing the plates in cyclohexane/ethyl acetate 1:1. The benzyl clavulanate was visualised by spraying with triphenyl tetrazolium chloride reagent. The $R_f$ was compared with that of an authentic sample of benzyl clavulanate chromatographed under the same conditions. (The triphenyl tetrazolium chloride reagent is prepared by mixing 1 part of a 4% methanolic triphenyl tetrazolium chloride solution with 1 part 1N caustic.

Fractions (30 - 45) containing benzyl clavulanate were combined and evaporated under reduced pressure to yield an oil.

The product from the Sephadex LH20 column was dissolved in a minimum of cyclohexane/ethyl acetate 1/1 and run onto a silica gel column (2.5 × 28 cm) (Merck silica gel H thin layer chromatography grade), prepared in the same solvent. The column was eluted with cyclohexane/ethyl acetate 1/1 and 28 fractions 7 ml in volume were collected followed by 15 ml fractions. Fractions (31-33) giving a red colour when spotted on silica gel thin layer chromatography plates and sprayed with triphenyl tetrazolium chloride reagent were combined and evaporated under reduced pressure.

The resulting oil was submitted for NMR and IR spectroscopy, the spectra were identical to those given by an authentic sample of benzyl clavulanate.

EXAMPLE 4

Preparation of Sodium Clavulanate

Benzyl clavulanate (0.5 g from Example 3) in ethanol (20ml) and water (5ml) was hydrogenated over 10% Pd/C (0.13 g) and sodium bicarbonate (0.15 g) for 25 minutes at room temperature and atmospheric pressure. The catalyst was filtered, washed with water and ethanol and the combined filtrates were evaporated in vacuo. The product crystallised from a water-acetone mixture as sodium clavulanate tetrahydate.

We claim:

1. A process for the preparation of clavulanic acid or a salt thereof which process comprises cultivating a strain of Streptomyces jumonjinensis and isolating clavulanic acid or a salt thereof from the culture.

2. A process according to claim 1 for the preparation of a solid lithium, sodium, potassium, calcium, magnesium, barium, aluminium, ammonium or substituted ammonium salt wherein a suitable source for said salt ion is present.

3. A process according to claim 2 for the preparation of the crystalline sodium clavulanate tetrahydrate salt, the crystalline potassium clavulanate salt or the crystalline lithium clavulanate salt wherein a suitable source of sodium, potassium or lithium is present.

4. A process according to claim 1 wherein a strain of Streptomyces jumonjinjensis is cultivated, thereafter the cells of Streptomyces jumonjinensis are removed from the fermentation and the resulting culture filtrate extracted to give clavulanic acid or a salt thereof.

5. A process according to claim 4 wherein clavulanic acid or a salt thereof is solvent extracted from the culture filtrate.

6. A process according to claim 5 wherein the culture filtrate is chilled, the pH of the culture filtrate is adjusted to a pH of 2 - 3 whereupon the clavulanic acid therein is first extracted into a water-immiscible organic solvent and then back extracted into aqueous sodium bicarbonate, potassium hydrogen phosphate buffer, calcium carbonate suspension or water with the pH maintained at approximate neutrality, and recovering clavulanic acid or a salt thereof from the resulting aqueous extract.

7. A process according to claim 5 wherein the culture filtrate is contacted with an organic phase in which is dissolved a water insoluble amine whereby clavulanic acid is extracted into the organic phase as the amine salt, and thereafter back-extracting clavulanic acid into an aqueous solution of an alkali metal salt and recovering clavulanic acid or a salt thereof from the aqueous extracts.

8. A process according to claim 4 wherein clavulanic acid or a salt thereof is extracted from the culture filtrate by methods based on the anionic nature of clavulanic acid.

9. A process according to claim 8 wherein the culture filtrate at pH 6 - 7 is contacted with a weak or strong base anion exchange resin until the resin becomes saturated with clavulanic acid and thereafter eluting with an aqueous salt solution and recovering a salt of clavulanic acid from the eluant.

10. A process according to claim 4 wherein an aqueous solution of the culture filtrate is passed through a charcoal bed then washed with water and eluted with an aqueous water miscible solvent.

11. A process according to claim 4 which process additionally comprises salting out or precipitating a water-insoluble salt of clavulanic acid.

12. A process according to claim 11 wherein the water insoluble salt of clavulanic acid is lithium clavulanate.

13. A process according to claim 11 wherein the precipitation is carried out by adding a water insoluble solvent to an aqueous solution of the relatively water insoluble salt of clavulanic acid.

14. A process according to claim 13 wherein the salting out of lithium clavulanate takes place in an aqueous solution of lithium clavulanate in the presence of an ionic lithium compound by raising the concentration of lithium ions in solution so that the solubility of lithium clavulanate at the temperature concerned is greatly exceeded.

15. A process according to claim 4 which process additionally comprises forming an ester of clavulanic acid in a conventional manner, purifying the ester and thereafter regenerating clavulanic acid or a salt thereof from the ester.

16. A process according to claim 15 wherein the ester of clavulanic acid is formed by the reaction of a salt of clavulanic acid with a reactive halide or sulphonate ester.

17. A process according to claim 16 wherein the reactive halide is benzyl bromide.

18. A process according to claim 15 wherein clavulanic acid or a salt thereof is regenerated from the ester by hydrogenolysis.

19. A process according to claim 4 which process additionally comprises further purification of clavulanic acid or a salt thereof by ion exchange column chromatography.

20. A process for the preparation of clavulanic acid or a salt thereof, which process comprises cultivating Streptomyces jumonjinensis NRRL 5741 or a high yielding mutant thereof, and isolating clavulanic acid or a salt thereof from the culture.

* * * * *